(12) United States Patent
Iijima et al.

(10) Patent No.: US 9,994,650 B2
(45) Date of Patent: Jun. 12, 2018

(54) METHOD FOR PRODUCING HYDROGENATED PETROLEUM RESIN

(71) Applicant: MARUZEN PETROCHEMICAL CO., LTD., Chuo-ku (JP)

(72) Inventors: Yoshikazu Iijima, Chiba (JP); Koichiro Kanai, Ichihara (JP); Yasunori Hayashi, Ichihara (JP); Takeshi Haruna, Chiba (JP)

(73) Assignee: MARUZEN PETROCHEMICAL CO., LTD., Chuo-ku (JP)

( * ) Notice: Subject to any disclaimer, the term of this patent is extended or adjusted under 35 U.S.C. 154(b) by 0 days. days.

(21) Appl. No.: 15/127,813

(22) PCT Filed: Mar. 25, 2015

(86) PCT No.: PCT/JP2015/059046
§ 371 (c)(1),
(2) Date: Sep. 21, 2016

(87) PCT Pub. No.: WO2015/147027
PCT Pub. Date: Oct. 1, 2015

(65) Prior Publication Data
US 2017/0096501 A1  Apr. 6, 2017

(30) Foreign Application Priority Data
Mar. 26, 2014 (JP) ................. 2014-062990

(51) Int. Cl.
C08F 8/04 (2006.01)
C08F 232/06 (2006.01)
C08F 32/04 (2006.01)
C07C 2/42 (2006.01)
C08F 212/08 (2006.01)
C07C 2/50 (2006.01)

(52) U.S. Cl.
CPC .................. *C08F 8/04* (2013.01); *C07C 2/42* (2013.01); *C07C 2/50* (2013.01); *C08F 32/04* (2013.01); *C08F 212/08* (2013.01); *C08F 232/06* (2013.01); *C07C 2602/42* (2017.05)

(58) Field of Classification Search
CPC .............................. C07C 13/42; B01F 5/0085
See application file for complete search history.

(56) References Cited

U.S. PATENT DOCUMENTS

| | | | | |
|---|---|---|---|---|
| 4,252,699 A * | 2/1981 | Tsuchiya | ............ | C08G 18/0804 260/DIG. 38 |
| 4,952,639 A * | 8/1990 | Minomiya | ................ | C08F 8/04 525/327.9 |
| 6,040,388 A | 3/2000 | Nishimura et al. | | |
| 6,232,418 B1 * | 5/2001 | Macedo | ................ | C08F 240/00 526/237 |

(Continued)

FOREIGN PATENT DOCUMENTS

| | | |
|---|---|---|
| EP | 1574526 | 9/2005 |
| JP | 63-20310 A | 1/1988 |
| JP | 2-51502 A | 2/1990 |
| JP | 2-289603 A | 11/1990 |

(Continued)

OTHER PUBLICATIONS

International Search Report dated Jun. 16, 2015 in PCT/JP2015/059046 Filed Mar. 25, 2015.
European Search Report as received in the corresponding European Patent No. 15768950.6 dated Oct. 9, 2017.

*Primary Examiner* — Robert C Boyle
(74) *Attorney, Agent, or Firm* — Oblon, McClelland, Maier & Neustadt, L.L.P.

(57) ABSTRACT

A method for producing a hydrogenated petroleum resin by reacting dicyclopentadiene with a vinyl aromatic compound, subjecting the reaction product obtained by this reaction to thermal polymerization, and then hydrogenating the resulting product, including the following steps (A) to (C):

(A) a preliminary reaction step of reacting a vinyl aromatic compound represented by the following Formula (1) (in the formula, $R^1$ is a hydrogen atom or the like) with dicyclopentadiene under the condition that selectivity for a phenylnorbornene derivative, which is a reaction product and is represented by the following Formula (2) {in the formula, $R^1$ has the same meaning as in the above Formula (1)}, is 90% or more to obtain a reaction liquid containing the phenylnorbornene derivative:

(B) a polymerization step of heating the reaction liquid, which contains the phenylnorbornene derivative and is obtained in the preliminary reaction step (A), to a temperature of 240 to 300° C. to polymerize the reaction liquid, thereby obtaining a polymerization reaction product; and (C) a hydrogenation step of hydrogenating the polymerization reaction product, which is obtained in the polymerization step (B), in the presence of a catalyst to obtain a hydrogenated petroleum resin.

(1)

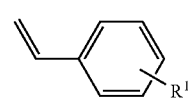

(2)

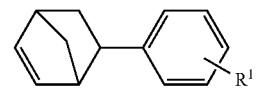

7 Claims, No Drawings

(56) References Cited

U.S. PATENT DOCUMENTS

| | | | |
|---|---|---|---|
| 6,294,706 B1 * | 9/2001 | Bergstrom | ............ C07C 13/42 |
| | | | 526/75 |
| 6,376,630 B1 | 4/2002 | Nishimura et al. | |
| 6,825,291 B2 * | 11/2004 | Klosiewicz | ............ C08F 8/04 |
| | | | 526/336 |
| 2002/0107332 A1 | 8/2002 | Klosiewicz et al. | |
| 2006/0063892 A1 | 3/2006 | Yamane | |
| 2006/0084773 A1 | 4/2006 | Fujioka | |
| 2014/0058033 A1 | 2/2014 | Kashima | |

FOREIGN PATENT DOCUMENTS

| | | |
|---|---|---|
| JP | 6-56920 A | 3/1994 |
| JP | 6-322020 A | 11/1994 |
| JP | 7-88412 B2 | 9/1995 |
| JP | 11-130820 A | 5/1999 |
| JP | 2004-515618 A | 5/2004 |
| JP | 2004-189764 A | 7/2004 |
| WO | 2004/003041 A1 | 1/2004 |
| WO | 2012/165522 A1 | 12/2012 |

* cited by examiner

METHOD FOR PRODUCING HYDROGENATED PETROLEUM RESIN

TECHNICAL FIELD

The present invention relates to a method for producing a hydrogenated petroleum resin, and more specifically to a method for producing a dicyclopentadiene/vinyl aromatic compound-based hydrogenated petroleum resin which is obtained by hydrogenating a thermal polymerization reaction product of dicyclopentadiene and a vinyl aromatic compound.

BACKGROUND ART

A dicyclopentadiene/vinyl aromatic compound-based hydrogenated petroleum resin obtained by hydrogenating the thermal polymerization reaction product of dicyclopentadiene and a vinyl aromatic compound is useful as a raw material of a hot-melt adhesive or the like (tackifier).

As the vinyl aromatic compound to be used in the thermal polymerization reaction, styrene is suitably used in terms of hue and adhesion providing property of the obtained resin. However, styrene has drawbacks that radicals are easily generated, a high-molecular-weight homopolymer is easily generated, and the obtained resin has a high molecular weight and is polydispersity.

As a method of suppressing an increase in molecular weight and polydispersion of the obtained resin, Patent Literature 1 proposes a method of adding a monomer mixed solution containing styrene and dicyclopentadiene to a heated solvent in a dropwise manner or in a divided manner to polymerize the resultant mixture (dropping polymerization method), and a resin having an Mw/Mn of 2.8 is obtained in Example. In addition, Patent Literature 2 discloses a two-stage polymerization method of performing post-polymerization at higher temperature after dropping polymerization, and a resin having an Mw/Mn of 2.7 is obtained in Example.

Patent Literature 3 describes that in a dropping polymerization method, a solvent to be introduced in advance is used at a ratio of 50 to 500 parts by weight with respect to total 100 parts by weight of a monomer to thereby obtain a resin having an Mw/Mn of 2.5 or less.

Further, Patent Literature 4 discloses that the concentration of styrene in a monomer mixed solution to be added dropwise is adjusted to about 5 to 25% by weight, and the addition rate is adjusted such that the concentration of free styrene monomer in the entire reaction mixture becomes less than about 5% by weight, thereby obtaining a resin having an Mz of less than 2000.

In these related arts, as a whole, a dropping polymerization method using a solvent is employed, and generation of a homopolymer of styrene was suppressed by decreasing the concentration of styrene in the reaction liquid. As a result, an increase in molecular weight and polydispersion can be suppressed.

However, in these dropping polymerization methods, use of a large amount of a solvent causes high cost. Further, since the yield of a resin per unit production amount is decreased due to use of the solvent, it is necessary to increase the size of an apparatus for mass production.

Regarding a solvent, Patent Literature 4 discloses that a solvent obtained by performing stripping treatment on a resin after polymerization can be recycled without any change. Further, Patent Literature 5 also proposes that a solvent is recovered and reused.

However, in order to perform the recycle of the solvent efficiently, it is necessary to use a monomer raw material which does not substantially contain a non-reacted component that is recovered together with the solvent and requires a separation step. Therefore, it is difficult to use, for example, an unrefined dicyclopentadiene fraction containing non-reacted components such as C5 and C6 olefins as a raw material. In addition, even in a case where a monomer raw material containing no non-reacted component is used, an unreacted monomer or oligomer or the like remaining in the solvent affects the adhesion providing property of the obtained resin. Therefore, a refining step of the solvent is necessary for reuse of the solvent, and thus an effect of reducing cost due to the recycle of the solvent is not too great.

On the other hand, as dicyclopentadiene to be used in the thermal polymerization reaction, generally, in addition to refined dicyclopentadiene with high purity or dicyclopentadiene, for example, a dicyclopentadiene fraction containing a codimer of cyclopentadiene and other dienes such as methyl cyclopentadiene, isoprene, and piperylene is used.

As to a production cost, for example, it is advantageous to use, as a raw material, an inexpensive unrefined dicyclopentadiene fraction further containing C5 and C6 paraffins and olefins, which is obtained by separating a thermally decomposed product such as naphtha. However, in the case of using an unrefined dicyclopentadiene fraction containing non-reacted components such as C5 and C6 paraffins, as described above, it is necessary to separate the non-reacted components at the time of recovering a polymerization solvent.

CITATION LIST

Patent Literature

Patent Literature 1: JP 07-88412 B
Patent Literature 2: JP 02-51502 A
Patent Literature 3: JP 11-130820 A
Patent Literature 4: JP 2004-515618 A
Patent Literature 5: JP 06-56920 A

DISCLOSURE OF INVENTION

Technical Problem

Further, the thermal polymerization reaction product achieves improvement in hue or compatibility by hydrogenation performed at the latter stage. However, according to the investigation of the present inventors, it found that in the case of using a raw material containing a large amount of impurities such as an unrefined dicyclopentadiene fraction containing C5 and C6 paraffins and olefins, the conventional dropping polymerization method is inferior in hue or compatibility of the resin after hydrogenation.

In order to improve hue of the resin, generally, it is necessary to perform hydrogenation under severer conditions. Meanwhile, when the hydrogenation conditions are severe, a nuclear hydrogenation rate of an aromatic component is also increased, and thus only a resin having poor compatibility is obtained. For this reason, it is necessary to adjust the aromatic content by performing polymerization using an excessively large amount of styrene with respect to a target aromatic content. However, use of a large amount of styrene as described above causes an increase in cost of a raw material, and hydrogenation under severe conditions is disadvantageous in terms of production efficiency and plant cost.

The present invention was made in view of such problems, and an objective thereof is to provide a novel method for producing a dicyclopentadiene/vinyl aromatic compound-based hydrogenated petroleum resin used as a tackifier, the method capable of suppressing an increase in molecular weight and polydispersion of a resin in thermal polymerization even when a solvent is not used, and, in addition, capable of producing the hydrogenated petroleum resin, which is advantageous in cost, without impairing hue and compatibility even when an unrefined dicyclopentadiene fraction is used as a raw material.

Solution to Problem

The present inventors conducted intensive studies to solve the above-described problems, and as a result, they found that when styrene and dicyclopentadiene are reacted with each other in advance under specific conditions to obtain a reaction liquid containing phenylnorbornene and the resulting reaction liquid was subjected to thermal polymerization, it is possible to obtain a resin in which an increase in molecular weight and polydispersion are suppressed without use of a solvent. The present inventors further conducted studies continuously, and thus the present invention has been completed.

That is, the present invention is to provide the following <1> to <4>.

<1> A method for producing a hydrogenated petroleum resin by reacting dicyclopentadiene with a vinyl aromatic compound, subjecting the reaction product obtained by this reaction to thermal polymerization, and then hydrogenating the reaction product, including the following steps (A) to (C):

(A) a preliminary reaction step of reacting a vinyl aromatic compound represented by the following Formula (1) with dicyclopentadiene under the condition that selectivity for a phenylnorbornene derivative, which is a reaction product and is represented by the following Formula (2), is 90% or more to obtain a reaction liquid containing the phenylnorbornene derivative:

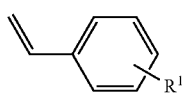

(1)

(in the formula, $R^1$ is a hydrogen atom, an alkyl group, a cycloalkyl group, an aryl group, or an aralkyl group), and

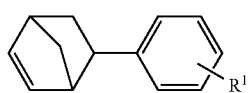

(2)

{in the formula, $R^1$ has the same meaning as in the above Formula (1)};

(B) a polymerization step of heating the reaction liquid, which contains the phenylnorbornene derivative and is obtained in the preliminary reaction step (A), to a temperature of 240 to 300° C. to polymerize the reaction liquid, thereby obtaining a polymerization reaction product; and (C) a hydrogenation step of hydrogenating the polymerization reaction product, which is obtained in the polymerization step (B), in the presence of a catalyst to obtain a hydrogenated petroleum resin.

<2> The method for producing a hydrogenated petroleum resin according to <1> described above, wherein in the preliminary reaction step (A), the reaction of a vinyl aromatic compound and dicyclopentadiene is performed in a temperature range of 170 to 190° C.

<3> The method for producing a hydrogenated petroleum resin according to <1> described above, wherein in the preliminary reaction step (A), a liquid containing a vinyl aromatic compound is added dropwise to dicyclopentadiene heated to a temperature of 170 to 190° C. to react a vinyl aromatic compound with dicyclopentadiene.

<4> The method for producing a hydrogenated petroleum resin according to <1> described above, wherein in the preliminary reaction step (A), a liquid containing a vinyl aromatic compound and dicyclopentadiene is added dropwise to dicyclopentadiene heated to a temperature of 170 to 190° C. to react a vinyl aromatic compound and dicyclopentadiene.

Advantageous Effects of Invention

According to the present invention, it is possible to produce a dicyclopentadiene/vinyl aromatic compound-based hydrogenated petroleum resin having suitable properties as a tackifier without use of a polymerization solvent, to suppress an increase in molecular weight and polydispersion of the resin in thermal polymerization, and to produce the resin, which is advantageous in cost, by using an inexpensive unrefined dicyclopentadiene fraction as a polymerization raw material.

DESCRIPTION OF EMBODIMENTS

A method for producing a hydrogenated petroleum resin of the present invention includes the above-described steps (A) to (C). Hereinafter, each step will be described in detail.

(A) Preliminary Reaction Step

In the preliminary reaction step, a vinyl aromatic compound represented by the above Formula (1) and dicyclopentadiene are reacted with each other under the condition that selectivity for a phenylnorbornene derivative, which is a reaction product and is represented by the above Formula (2), is 90% or more to obtain a reaction liquid containing the phenylnorbornene derivative.

In the above Formula (1) and Formula (2), $R^1$ represents a hydrogen atom, an alkyl group, a cycloalkyl group, an aryl group, or an aralkyl group, and is preferably a hydrogen atom.

The alkyl group represented by $R^1$ is preferably an alkyl group having 1 to 10 carbon atoms and more preferably an alkyl group having 1 to 7 carbon atoms. In addition, the alkyl group may be linear or branched, and examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, an n-hexyl group, an isohexyl group, and an n-heptyl group.

In addition, the cycloalkyl group is preferably a cycloalkyl group having 3 to 7 carbon atoms. Examples thereof include a cyclopentyl group, a cyclohexyl group, and a cycloheptyl group.

In addition, examples of the aryl group include aryl groups having 6 to 12 carbon atoms such as a phenyl group, a tolyl group, a xylyl group, and a naphthyl group. Further, examples of the aralkyl group include aralkyl groups having 7 to 20 carbon atoms such as a benzyl group, a phenethyl group, and a naphthylmethyl group.

Specific examples of the vinyl aromatic compound to be used in the present invention include styrene, p-methylstyrene, and p-tert-butylstyrene. The vinyl aromatic compound is preferably styrene. Note that a stabilizer such as a polymerization inhibitor may be included in the vinyl aromatic compound.

The dicyclopentadiene to be used in the preliminary reaction step is not particularly limited, and high-purity dicyclopentadiene or an unrefined dicyclopentadiene fraction, which contains approximately 40 to 100% by mass of dicyclopentadiene; approximately 0 to 30% by mass of a codimer of cyclopentadiene and other dienes (methyl cyclopentadiene and isoprene, piperylene, or the like) (hereinafter, referred to as "C10+" in some cases); approximately 0 to 40% by mass of C5 and C6 paraffins; and approximately 0 to 20% by mass of C5 and C6 olefins, can be used as a dicyclopentadiene raw material. In addition, a mixture of dicyclopentadiene and cyclopentadiene can also be used.

Among such dicyclopentadiene raw materials, in terms of the yield of a resin to be obtained by thermal polymerization, it is preferable to use those having a high concentration of a reactive component, such as dicyclopentadiene and a codimer. Meanwhile, in the present invention, an unrefined dicyclopentadiene fraction, which is inexpensive and contains non-reactive components such as C5 and C6 paraffins, can also be used.

As the dicyclopentadiene fraction containing C5 and C6 paraffins, a dicyclopentadiene fraction containing 50 to 85% by mass of dicyclopentadiene and 5 to 30% by mass in total of C5 and C6 paraffins is preferable, and a dicyclopentadiene fraction containing 60 to 80% by mass of dicyclopentadiene and 10 to 25% by mass in total of C5 and C6 paraffins is more preferable. Note that the balance includes other components (for example, C5 and C6 olefins and C10+) of the dicyclopentadiene fraction.

Further, the preliminary reaction step of the present invention can be performed without use of a reaction solvent.

Note that when an unrefined dicyclopentadiene fraction, which is obtained from a thermal decomposition apparatus, such as naphtha is used, the concentration of dicyclopentadiene significantly varies depending on an operation. For this reason, in order to keep the quality of the resin between lots uniform, a composition may be adjusted by adding a solvent to the dicyclopentadiene fraction. In this case, the solvent is used for adjusting the composition and the used amount thereof may be extremely small as compared with the conventional method in which the solvent is used as a polymerization solvent. In general, the used amount thereof is 10% by mass or less with respect to the dicyclopentadiene fraction.

As such a solvent, for example, an aromatic solvent such as benzene, toluene, or xylene; or a napthenic solvent such as cyclohexane, dimethylcyclohexane, or ethylcyclohexane can be suitably used.

Further, in the preliminary reaction step, it is important that the phenylnorbornene derivative is generated and a polymer, including a homopolymer of the vinyl aromatic compound, is generated in a small amount (preferably, such polymer is not substantially generated). Therefore, selectivity for the phenylnorbornene derivative in the preliminary reaction step is preferably 90% or more, more preferably 95% or more, even more preferably 97% or more, and particularly preferably 99% or more.

When the vinyl aromatic compound and dicyclopentadiene are reacted with each other at such high selectivity for the phenylnorbornene derivative, surprisingly, it is possible to suppress an increase in molecular weight and polydispersion of the resin in the latter polymerization step even when an unreacted vinyl aromatic compound remains after the completion of the preliminary reaction step. Therefore, the conversion rate of the vinyl aromatic compound in the preliminary reaction step is not necessary to be so high, and may be approximately 50% or more.

Note that the conversion rate of the vinyl aromatic compound and the selectivity for the phenylnorbornene derivative are calculated by the following equation. In addition, the residual amount of the vinyl aromatic compound and the generated amount of the phenylnorbornene derivative can be generally obtained by gas chromatography.

Conversion rate (%)=[[Charged amount (mol) of vinyl aromatic compound−Residual amount (mol) of vinyl aromatic compound]/[Charged amount (mol) of vinyl aromatic compound]×100

Selectivity (%)=[[Generated amount (mol) of phenylnorbornene derivative]/[Charged amount (mol) of vinyl aromatic compound−Residual amount (mol) of vinyl aromatic compound]]×100

In order to allow the vinyl aromatic compound and dicyclopentadiene to be reacted with each other at such high selectivity of the phenylnorbornene derivative, it is preferable to react the vinyl aromatic compound and dicyclopentadiene in a temperature range of 170 to 190° C. When the reaction temperature is set to 170° C. or higher, dicyclopentadiene is thermally decomposed sufficiently and the reaction easily proceeds. Therefore, the phenylnorbornene derivative is efficiently generated. In addition, when the reaction temperature is set to 190° C. or lower, an increase in molecular weight caused by the reaction of the phenylnorbornene derivative or generation of a homopolymer of the vinyl aromatic compound is suppressed, and thus the selectivity for the phenylnorbornene derivative is enhanced.

Further, from the viewpoint that the concentration of the vinyl aromatic compound in the reaction system is adjusted to low and the generation of a homopolymer of the vinyl aromatic compound is suppressed, it is preferable to perform reaction by adding a liquid containing a vinyl aromatic compound dropwise to dicyclopentadiene heated to the above-described temperature range (in a divided manner or a continuous manner).

Specifically, it is preferable to perform reaction in such a manner that, after a predetermined amount of dicyclopentadiene is charged into a reaction vessel in advance and the reaction vessel is heated to the above-described reaction temperature, while the temperature thereof is maintained, a liquid containing a vinyl aromatic compound is added dropwise thereto in a divided manner or a continuous manner.

The liquid to be added dropwise may contain only the vinyl aromatic compound or may contain the vinyl aromatic compound and dicyclopentadiene. As this dicyclopentadiene, the dicyclopentadiene raw material described above can be used. Further, dicyclopentadiene to be charged into a reaction vessel in advance and dicyclopentadiene to be used in a dropping liquid may have the same composition or different composition.

The ratio of the used amounts of dicyclopentadiene to be charged into a reaction vessel in advance and the dropping liquid and the ratio of the used amounts of the vinyl aromatic compound and dicyclopentadiene in the dropping liquid in a case where the dropping liquid contains dicyclopentadiene are appropriately set depending on a target value of the aromatic content of a resin to be obtained. They are preferably in a range of 20 to 150 parts by mass of the dropping liquid with respect to 100 parts by mass of the charged amount into the reaction vessel. When the used amount of the dropping liquid is set to 20 parts by mass or more, the aromatic content of the resin to be obtained becomes sufficient. In addition, when the used amount of the dropping liquid is set to 150 parts by mass or less, the concentration of the vinyl aromatic compound at the time of dropwise addition becomes low, and a local increase in temperature due to reaction heat is suppressed. Therefore, a decrease in selectivity for the phenylnorbornene derivative can be prevented.

Further, the ratio (mass ratio) of the vinyl aromatic compound and the entire dicyclopentadiene, which is supplied to the reaction system, can be appropriately selected depending on a target value of the aromatic content of a resin to be obtained, and is generally 5/95 to 60/40, preferably 10/90 to 50/50, more preferably 15/85 to 40/60, and particularly preferably 20/80 to 30/70.

The period of time for dropwise addition is preferably 1 to 4 hours. When the dropping time is set to 1 hour or longer, the concentration of the vinyl aromatic compound in the reaction liquid system becomes low and a rapid increase in temperature due to reaction heat is suppressed. Therefore, a decrease in selectivity for the phenylnorbornene derivative can be prevented. According to this, a homopolymer is difficult to generate in the subsequent polymerization step. In addition, when the dropping time is set to 4 hours or shorter, homopolymerization of cyclopentadiene is difficult to proceed. Therefore, a polymer is difficult to form in the subsequent polymerization step.

Further, it is preferable to perform the reaction at the time of dropwise addition while the inside of the system is stirred such that the temperature in the reaction vessel is uniformly maintained and the concentration of the vinyl aromatic compound is not locally increased.

(B) Polymerization Step

In the polymerization step, the reaction liquid containing the phenylnorbornene derivative obtained in the preliminary reaction step (A) is heated to a temperature of 240 to 300° C. to perform thermal polymerization. When the polymerization temperature is lower than 240° C., the polymerization rate is significantly decreased. In addition, when the polymerization temperature is increased to higher than 300° C., the polymerization rate is significantly increased.

The polymerization temperature is preferably 250 to 280° C. from the viewpoint of the polymerization rate. Note that the polymerization time is preferably 0.5 to 4 hours and more preferably 1 to 3 hours.

The thermal polymerization can be carried out in the absence of a solvent, and can be performed by heating the reaction liquid to the polymerization temperature while the reaction liquid is held in the reaction vessel used in the preliminary reaction step. Further, the thermal polymerization may also be performed by transferring the obtained reaction liquid to another polymerization vessel.

When the reaction vessel used in the preliminary reaction step is heated to the polymerization temperature, a temperature rising rate is preferably 1.5° C./min or more in terms of preventing an increase in molecular weight of a resin to be obtained by thermal polymerization.

(C) Hydrogenation Step

In the hydrogenation step, the polymerization reaction product obtained in the polymerization step (B) is hydrogenated in the presence of a catalyst to obtain a hydrogenated petroleum resin.

The polymerization reaction product may be provided to the hydrogenation step without any changes, or may be provided to the hydrogenation step after an unreacted monomer component and a low-molecular-weight polymer in the obtained polymerization reaction product are removed. The method of separating or removing, for example, the monomer component is not particularly limited, and for example, a flash distillation apparatus or a thin film evaporator can be suitably used.

There is no limitation on the method for hydrogenating the polymerization reaction product, and for example, a batch reaction apparatus or a continuous flow reaction apparatus can be used.

In the case of using a batch reaction apparatus, regarding the reaction conditions, a temperature is generally 200 to 300° C. and preferably 200 to 270° C., a reaction pressure is generally 0 to 10 MPaG (G represents a gauge pressure. The same applies hereinafter.) and preferably 1 to 7 MPaG, and a reaction time is generally 0.5 to 8 hours and preferably 1 to 5 hours.

Further, in the case of using a continuous flow reaction apparatus, a fixed bed flow reactor can be generally used and a trickle flow reactor using a liquid-gas co-current can be preferably used. Regarding the reaction conditions, a temperature is generally 100 to 300° C. and preferably 120 to 250° C., a reaction pressure is generally 0 to 10 MPaG and preferably 1 to 5 MPaG, and an LHSV (liquid hourly space velocity) is generally 2.0 to 12.0 [$h^{-1}$] and preferably 5.0 to 12.0 [$h^{-1}$]. Note that the number of the flow reactors is not particularly limited, and hydrogenation in a divided manner by using two or more towers of the flow reactor can also be carried out.

As a catalyst to be used in the hydrogenation step, generally, known catalysts such as nickel, palladium, cobalt, platinum, and rhodium-based catalysts can be suitably used, and a nickel-based or palladium-based catalyst is preferable. In terms of hue of the hydrogenated petroleum resin, a palladium-based catalyst is more preferable.

Specific examples of the catalyst include catalysts of transition metals represented by, for example, nickel, palladium, cobalt, platinum, and rhodium; and those having these supported on any carrier. Examples of the carrier include alumina, silica, silica-alumina, zeolite, clay mineral (for example, montmorillonite), and silicon carbide.

Further, the reaction in the hydrogenation step may be performed in the presence of a solvent. Examples of this solvent include napthenic solvents such as cyclohexane, dimethylcyclohexane, and ethylcyclohexane.

A target hydrogenated petroleum resin can be obtained by removing a volatile content, such as an unreacted monomer component, a low-molecular-weight polymer, or a solvent, from the hydrogenated petroleum resin obtained in the hydrogenation step, as necessary. The method of separating or removing, for example, a monomer component is not particularly limited, and for example, a flash distillation apparatus or a thin film evaporator can be suitably used.

EXAMPLES

Hereinafter, the present invention will be described in more detail by means of Examples, and the present invention is not limited thereto. Note that in Examples, for example, compositions are by mass unless otherwise specified.

Further, the gas chromatography analysis of the reaction liquid was performed using n-dodecane as an internal standard under the following conditions.

Analyzer: GC-14A (manufactured by SHIMADZU CORPORATION)

Detector: FID (hydrogen flame ionization detector)

Column used: TC-1 (inner diameter: 0.25 mm, length: 60 m, film thickness: 0.25 μm)

Analysis condition: maintaining a state where an injection temperature is 250° C. and a column temperature is 40° C. for 5 minutes, then increasing a temperature at 10° C./min, and maintaining at 70° C. for 22 minutes, at 200° C. for 10 minutes, and at 280° C. for 9 minutes, respectively, detector temperature: 250° C.

For example, properties of the obtained resin were measured by the following methods.

(1) Molecular Weight Measurement

Molecular weights (weight average molecular weight Mw, number average molecular weight Mn, and Z average molecular weight Mz) and molecular weight distribution (Mw/Mn) were calculated as a value in terms of polystyrene by using a high-speed GPC apparatus (manufactured by Tosoh Corporation, HLC-8320GPC) [Eluent: tetrahydrofuran, Column: G4000HXL, G3000HXL, and G2000HXL (two columns) manufactured by Tosoh Corporation were connected in series and used, Detector: RI, Standard sample: polystyrene].

(2) Softening Point Measurement

The softening point was measured by a ring-and-ball method in accordance with JIS K-2207(1991).

(3) Cloud Point Measurement

A hydrogenated resin and an ethylene-vinyl acetate copolymer (manufactured by DuPont-Mitsui, product name "Everflex EVA-210") were mixed and dissolved at a ratio of 50/50 (mass ratio), and measurement was carried out in accordance with JIS K-2269 "Testing Method for Cloud Point of Petroleum Products." As the cloud point is low, compatibility between the hydrogenated resin and the ethylene-vinyl acetate copolymer is high.

(4) Aromatic Content Rate

The aromatic content rate was calculated from the measurement result of $^1$H-NMR spectrum.

(5) Hue (Hazen color number)

The hue was measured by preparing 50% by mass of toluene solution and using a colorimeter (Lovibond PFX195 manufactured by Tintometer GmbH).

(6) Yield

The yield of the resin in the thermal polymerization was calculated by the following equation.

Yield (% by mass)=[Resin yield (g)/Total charged amount (g)]×100

Herein, the total charged amount is the total amount of a dicyclopentadiene fraction and styrene incorporated into a reaction vessel, and in the case of using a solvent, also includes the solvent.

Example 1: Production Example (1) of Hydrogenated Resin (Preliminary Reaction Step)

In an autoclave having an internal capacity of 10 L and equipped with a stirrer, 2593 g of dicyclopentadiene fraction X having the composition presented in Table 1 (dicyclopentadiene concentration: 75% by mass) was charged, and the inside of the system was replaced with nitrogen. Thereafter, the temperature was increased to 180° C. at a rate of 4° C./min while stirring at 500 rpm. A mixed solution of 970 g of styrene and 1439 g of the dicyclopentadiene fraction X was added dropwise thereto over 2 hours while the temperature was maintained at 180° C.

The reaction liquid at the time of completion of drop addition was analyzed by gas chromatography, and as a result, it found that the conversion rate of styrene was 58%, the selectivity for phenylnorbornene was 100%, and the polymer derived from styrene was not generated at all.

(Polymerization Step)

The reaction liquid after the completion of drop addition was heated to 260° C. at a rate of 1.8° C./min, followed by heated at 260° C. for 2 hours to perform polymerization reaction. Therefore, a polymerization reaction product 1 was obtained.

A part of the polymerization reaction product 1 was fractionated, and treated by using a rotary evaporator for 10 minutes at a temperature of 230° C. under a nitrogen gas stream to remove the unreacted monomer. Subsequently, treatment was performed for 15 minutes at a temperature of 230° C. and a pressure of 6.7 kPaA (A represents an absolute pressure. The same applies hereinafter.) to remove a part of the low-molecular-weight body, thereby obtaining a resin P1. The properties of the resin P1 are presented in Table 2.

(Hydrogenation Step)

Hydrogenation with a nickel-based catalyst was performed using the polymerization reaction product 1 obtained in the polymerization step to obtain a hydrogenated resin Q1. That is, into an autoclave having an internal capacity 1 L and equipped with a stirrer, 500 g of the polymerization reaction product 1 and 0.75 g of nickel-supported silica, alumina catalyst were charged, the inside of the system was replaced with nitrogen, and hydrogenation reaction was performed for 1.5 hours at a temperature of 230° C. and a hydrogen pressure of 3 MPaG.

After the hydrogenation reaction, treatment was performed using a rotary evaporator for 10 minutes at a temperature of 230° C. under a nitrogen gas stream to remove the unreacted monomer. Subsequently, treatment was performed for 10 minutes at a temperature of 230° C. and a pressure of 6.7 kPaA to remove a part of the low-molecular-weight body, thereby obtaining a hydrogenated resin Q1. The properties of the hydrogenated resin Q1 are presented in Table 3.

Comparative Example 1: Production Example (2) of Hydrogenated Resin

Comparative Example in a case where the selectivity for phenylnorbornene in the preliminary reaction step is less than 90% (in a case where the reaction temperature is high) will be described.

(Preliminary Reaction Step)

The preliminary reaction was performed under the same conditions as in Example 1, except that the reaction was performed at a temperature of 210° C. The reaction liquid at the time of completion of drop addition was analyzed by gas chromatography, and as a result, it found that the conversion rate of styrene was 82%, the selectivity for phenylnorbornene was 82%, and the selectivity was decreased although the generated amount of phenylnorbornene was larger than that in Example 1.

(Polymerization Step)

Subsequently, the polymerization reaction was performed in the same manner as in Example 1 to obtain a polymerization reaction product 2. A part of the polymerization reaction product 2 was fractionated, and treated by using a rotary evaporator for 10 minutes at a temperature of 230° C. under a nitrogen gas stream to remove the unreacted monomer. Subsequently, treatment was performed for 5 minutes at a temperature of 230° C. and a pressure of 6.7 kPaA to remove a part of the low-molecular-weight body, thereby obtaining a resin P2. The properties of the resin P2 are presented in Table 2.

The Z average molecular weight (Mz) and the molecular weight distribution (Mw/Mn) of the obtained resin P2 were much increased as compared with Example 1 using the same dicyclopentadiene fraction X as a raw material, and in a case where the selectivity was less than 90% although the generated amount of phenylnorbornene in the preliminary reaction step was large, an increase in molecular weight and polydispersion of the resin occurred.

(Hydrogenation Step)

Hydrogenation with a nickel-based catalyst was performed using the polymerization reaction product 2 obtained in the polymerization step to obtain a hydrogenated resin Q2. That is, into an autoclave having an internal capacity 1 L and equipped with a stirrer, 500 g of the polymerization reaction product 2 and 0.75 g of nickel-supported silica•alumina catalyst were charged, the inside of the system was replaced with nitrogen, and hydrogenation reaction was performed for 3 hours at a temperature of 230° C. and a hydrogen pressure of 3 MPaG.

After the hydrogenation reaction, treatment was performed using a rotary evaporator for 10 minutes at a temperature of 230° C. under a nitrogen gas stream to remove the unreacted monomer. Subsequently, treatment was performed for 8 minutes at a temperature of 230° C. and a pressure of 6.7 kPaA to remove a part of the low-molecular-weight body, thereby obtaining a hydrogenated resin Q2. The properties of the hydrogenated resin Q2 are presented in Table 3.

The hue and the compatibility (cloud point) of the obtained hydrogenated resin Q2 were much inferior to the hydrogenated resin Q1.

Comparative Example 2: Production Example (3) of Hydrogenated Resin

Comparative Example obtained by the conventional dropping polymerization method (that is, a method of adding a monomer solution dropwise to a heated solvent) will be described.

(Dropping Polymerization Step)

Into an autoclave having an internal capacity of 10 L and equipped with a stirrer, 300 g of xylene was charged, and the inside of the system was replaced with nitrogen. Thereafter, the temperature was increased to 240° C. at a rate of 4° C./min while stirring at 500 rpm. A mixed solution of 478 g of styrene and 2022 g of the dicyclopentadiene fraction X was added dropwise thereto over 2 hours while the temperature was maintained at 240° C. so as to perform polymerization reaction.

After the completion of drop addition, the reaction liquid was heated to 260° C. at a rate of 1.8° C./min, followed by heated at 260° C. for 2 hours to promote polymerization reaction. Therefore, a polymerization reaction product 3 was obtained.

A part of the polymerization reaction product 3 was fractionated, and treated by using a rotary evaporator for 10 minutes at a temperature of 230° C. under a nitrogen gas stream to remove the unreacted monomer. Subsequently, treatment was performed for 3 minutes at a temperature of 230° C. and a pressure of 6.7 kPaA to remove a part of the low-molecular-weight body, thereby obtaining a resin P3. The properties of the resin P3 are presented in Table 2.

The Z average molecular weight (Mz) and the molecular weight distribution (Mw/Mn) of the obtained resin P3 were the same level as those of Example 1 using the same dicyclopentadiene fraction X as a raw material.

(Hydrogenation Step)

Hydrogenation with a nickel-based catalyst was performed using the polymerization reaction product 3 obtained in the dropping polymerization step to obtain a hydrogenated resin Q3. That is, into an autoclave having an internal capacity 1 L and equipped with a stirrer, 500 g of the polymerization reaction product 3 and 0.75 g of nickel-supported silica•alumina catalyst were charged, the inside of the system was replaced with nitrogen, and hydrogenation reaction was performed for 1.5 hours at a temperature of 230° C. and a hydrogen pressure of 3 MPaG.

After the hydrogenation reaction, treatment was performed using a rotary evaporator for 10 minutes at a temperature of 230° C. under a nitrogen gas stream to remove the unreacted monomer. Subsequently, treatment was performed for 10 minutes at a temperature of 230° C. and a pressure of 6.7 kPaA to remove a part of the low-molecular-weight body, thereby obtaining a hydrogenated resin Q3. The properties of the hydrogenated resin Q3 are presented in Table 3.

The hue and the compatibility (cloud point) of the obtained hydrogenated resin Q3 were inferior to Example 1 in which hydrogenation was performed under the same conditions.

Example 2: Production Example (4) of Hydrogenated Resin (Hydrogenation Step)

Hydrogenation with a palladium-based catalyst was performed using the same polymerization reaction product 1 as in Example 1 to obtain a hydrogenated resin Q4. That is, into an autoclave having an internal capacity 1 L and equipped with a stirrer, 500 g of the polymerization reaction product 1 and 1.5 g of palladium-supported alumina catalyst were charged, the inside of the system was replaced with nitrogen, and hydrogenation reaction was performed for 5 hours at a temperature of 265° C. and a hydrogen pressure of 5 MPaG.

After the hydrogenation reaction, treatment was performed using a rotary evaporator for 10 minutes at a temperature of 230° C. under a nitrogen gas stream to remove the unreacted monomer. Subsequently, treatment was performed for 8 minutes at a temperature of 230° C. and a pressure of 6.7 kPaA to remove a part of the low-molecular-weight body, thereby obtaining a hydrogenated resin Q4. The properties of the hydrogenated resin Q4 are presented in Table 3.

Example 3: Production Example (5) of Hydrogenated Resin (Preliminary Reaction Step)

Into an autoclave having an internal capacity of 10 L and equipped with a stirrer, 3600 g of dicyclopentadiene fraction Y having the composition presented in Table 1 (dicyclopentadiene concentration: 71% by mass) was charged, and the inside of the system was replaced with nitrogen. Thereafter, the temperature was increased to 180° C. at a rate of 4° C./min while stirring at 500 rpm. A mixed solution of 1014 g of styrene and 986 g of the dicyclopentadiene fraction Y was added dropwise thereto over 2 hours while the temperature was maintained at 180° C.

(Polymerization Step)

After the completion of drop addition, the reaction liquid was heated to 260° C. at a rate of 1.8° C./min, followed by heated at 260° C. for 2 hours to perform polymerization reaction. Therefore, a polymerization reaction product 4 was obtained.

The polymerization reaction product 4 was treated by using a rotary evaporator for 10 minutes at a temperature of 230° C. under a nitrogen gas stream to remove the unreacted monomer. Subsequently, treatment was performed for 8 minutes at a temperature of 230° C. and a pressure of 6.7 kPaA to remove a part of the low-molecular-weight body, thereby obtaining a resin P4. The properties of the resin P4 are presented in Table 2.

(Hydrogenation Step)

Two-stage continuous hydrogenation with a palladium-based catalyst was performed by using the obtained resin P4 to obtain a hydrogenated resin Q5. That is, the resin P4 was dissolved in ethylcyclohexane to prepare a resin solution having a resin concentration of 20% by mass, the solution was allowed to pass through a fixed bed flow reactor (gas-liquid co-current, downflow type) filled with a palladium-supported alumina catalyst, and then hydrogenation reaction was performed at a temperature of 120° C., a hydrogen pressure of 1 MPaG, and an LHSV of 5.6 [h$^{-1}$]. Further, using the same fixed bed flow reactor, hydrogenation reaction was performed at a temperature of 220° C., a hydrogen pressure of 1 MPaG, and an LHSV of 10.9 [h$^{-1}$].

After the hydrogenation reaction, the reaction liquid was taken out, and treatment was performed by using a rotary evaporator for 20 minutes at a temperature of 180° C. under a nitrogen gas stream to remove the solvent. Subsequently, treatment was performed for 10 minutes at a temperature of 180° C. and a pressure of 6.7 kPaA to remove a part of the low-molecular-weight body, thereby obtaining a hydrogenated resin Q5. The properties of the hydrogenated resin Q5 are presented in Table 3.

Example 4: Production Example (6) of Hydrogenated Resin (Preliminary Reaction Step)

Into an autoclave having an internal capacity of 5 L and equipped with a stirrer, 1800 g of dicyclopentadiene fraction Z having the composition presented in Table 1 (dicyclopentadiene concentration: 60% by mass) was charged, and the inside of the system was replaced with nitrogen. Thereafter, the temperature was increased to 180° C. at a rate of 4° C./min while stirring at 500 rpm. A mixed solution of 445.2 g of styrene and 554.8 g of the dicyclopentadiene fraction Z was added dropwise thereto over 2 hours while the temperature was maintained at 180° C.

(Polymerization Step)

After the completion of drop addition, the reaction liquid was heated to 260° C. at a rate of 1.8° C./min, followed by heated at 260° C. for 2 hours to perform polymerization reaction. Therefore, a polymerization reaction product 5 was obtained.

A part of the polymerization reaction product 5 was fractionated, and treated by using a rotary evaporator for 10 minutes at a temperature of 230° C. under a nitrogen gas stream to remove the unreacted monomer. Subsequently, treatment was performed for 12 minutes at a temperature of 230° C. and a pressure of 6.7 kPaA to remove a part of the low-molecular-weight body, thereby obtaining a resin P5. The properties of the resin P5 are presented in Table 2.

(Hydrogenation Step)

Hydrogenation with a palladium-based catalyst was performed using the polymerization reaction product 5 obtained in the polymerization step to obtain a hydrogenated resin Q6. That is, into an autoclave having an internal capacity 1 L and equipped with a stirrer, 500 g of the polymerization reaction product 5 and 1.5 g of palladium-supported alumina catalyst were charged, the inside of the system was replaced with nitrogen, and hydrogenation reaction was performed for 5 hours at a temperature of 255° C. and a hydrogen pressure of 5 MPaG.

After the hydrogenation reaction, treatment was performed using a rotary evaporator for 10 minutes at a temperature of 230° C. under a nitrogen gas stream to remove the unreacted monomer. Subsequently, treatment was performed for 8 minutes at a temperature of 230° C. and a pressure of 6.7 kPaA to remove a part of the low-molecular-weight body, thereby obtaining a hydrogenated resin Q6. The properties of the hydrogenated resin Q6 are presented in Table 3.

TABLE 1

| Composition [% by mass] | Dicyclopentadiene fraction | | |
|---|---|---|---|
| | X | Y | Z |
| Dicyclopentadiene | 75 | 71 | 60 |
| C5 and C6 paraffins | 12 | 12 | 23 |
| C5 and C6 olefins | 5 | 5 | 10 |
| C10+ (codimer or the like) | 7 | 9 | 5 |
| Others | 1 | 3 | 2 |

TABLE 2

| | Example 1 | Comparative Example 1 | Comparative Example 2 | Example 3 | Example 4 |
|---|---|---|---|---|---|
| Raw material DCPD fraction | X | X | X | Y | Z |
| St/DCPD [mass ratio] | 24/76 | 24/76 | 24/76 | 23/77 | 24/76 |
| Thermally polymerized resin | P1 | P2 | P3 | P4 | P5 |
| Softening point [° C.] | 82 | 80 | 84 | 81 | 79 |
| Mz | 1896 | 2141 | 1946 | 1849 | 1627 |
| Mw/Mn | 2.25 | 2.44 | 2.27 | 2.26 | 2.07 |
| Yield [% by mass] | 79.3 | 82.5 | 73.8 | 78.2 | 61.9 |

DCPD: dicyclopentadiene
St: styrene

TABLE 3

| | Example 1 | Comparative Example 1 | Comparative Example 2 | Example 2 | Example 3 | Example 4 |
|---|---|---|---|---|---|---|
| Catalyst | Ni-based | Ni-based | Ni-based | Pd-based | Pd-based | Pd-based |
| Hydrogenated resin | Q1 | Q2 | Q3 | Q4 | Q5 | Q6 |
| Softening point [° C.] | 105 | 101 | 105 | 100 | 98 | 100 |
| Aromatic content rate [%] | 7.4 | 10.3 | 9.5 | 10.0 | 6.0 | 9.4 |
| Cloud point [° C.] | 35 | 220 or more | 110 | 35 | 35 | 35 |
| HZ | 1830 | 2030 | 1916 | 1990 | 1850 | 1770 |
| Mw/Mn | 2.46 | 2.75 | 2.18 | 2.30 | 2.21 | 2.20 |
| Hue [Hazen No.] | 69 | 342 | 168 | 36 | 13 | 25 |

As shown in Examples 1 to 4, according to the production method of the present invention, an increase in molecular weight and polydispersion in thermal polymerization can be suppressed without use of a solvent, and a hydrogenated petroleum resin with excellent hue and compatibility is obtained even in a case where an unrefined dicyclopentadiene fraction is used.

Therefore, according to the production method of the present invention, a hydrogenated petroleum resin suitable as a tackifier can be produced at low cost.

The invention claimed is:

1. A method for producing a hydrogenated petroleum resin, the method comprising:
   (A) preliminarily reacting a vinyl aromatic compound represented by the following Formula (1) with dicyclopentadiene, which comprises 50 to 85% by mass of dicyclopentadiene and 5 to 30% by mass in total of C5 and C6 paraffins, at a temperature of from 170 to 190° C. to yield a reaction liquid consisting of phenylnorbornene derivative represented by the following Formula (2), wherein the vinyl aromatic compound and the dicyclopentadiene are in a mass ratio of from 15/85 to 40/60:

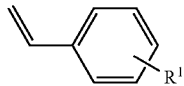

(1)

wherein $R^1$ is a hydrogen atom, an alkyl group, a cycloalkyl group, an aryl group, or an aralkyl group, and

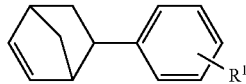

(2)

wherein $R^1$ has the same meaning as in the above Formula (1);
   (B) polymerizing the reaction liquid by heating the reaction liquid obtained in the preliminary reacting to a temperature of 240 to 300° C. to polymerize the reaction liquid, thereby obtaining a polymerization reaction product; and
   (C) hydrogenating the polymerization reaction product in the presence of a catalyst to obtain a hydrogenated petroleum resin.

2. The method for producing a hydrogenated petroleum resin according to claim 1, wherein in the preliminary reacting in (A), a liquid containing a vinyl aromatic compound is added dropwise to dicyclopentadiene heated to a temperature of 170 to 190° C. to react a vinyl aromatic compound with dicyclopentadiene.

3. The method for producing a hydrogenated petroleum resin according to claim 1, wherein in the preliminary reacting in (A), a liquid containing a vinyl aromatic compound and dicyclopentadiene is added dropwise to dicyclopentadiene heated to a temperature of 170 to 190° C. to react a vinyl aromatic compound and dicyclopentadiene.

4. The method for producing a hydrogenated petroleum resin according to claim 1, wherein the selectivity in (A) is 97% or more.

5. The method for producing a hydrogenated petroleum resin according to claim 1, wherein the selectivity in (A) is 99% or more.

6. The method for producing a hydrogenated petroleum resin according to claim 1, which is conducted in the absence of polymerization solvent.

7. The method for producing a hydrogenated petroleum resin according to claim 1, wherein the dicyclopentadiene is an unrefined dicyclopentadiene fraction.

* * * * *